United States Patent
Glasbey et al.

(10) Patent No.: US 8,109,064 B2
(45) Date of Patent: Feb. 7, 2012

(54) METHODS AND SYSTEMS FOR CONTACT LENS STERILIZATION

(75) Inventors: Trevor Glasbey, Singapore (SG); Stephen D. Newman, Singapore (SG)

(73) Assignee: Menicon Signapore Pte Ltd., Singapore (SG)

(*) Notice: Subject to any disclaimer, the term of this patent is extended or adjusted under 35 U.S.C. 154(b) by 0 days.

(21) Appl. No.: 11/654,786

(22) Filed: Jan. 18, 2007

(65) Prior Publication Data

US 2007/0163210 A1  Jul. 19, 2007

Related U.S. Application Data

(60) Provisional application No. 60/759,735, filed on Jan. 18, 2006.

(51) Int. Cl.
*B65B 55/22* (2006.01)

(52) U.S. Cl. .................. 53/431; 53/111 RC

(58) Field of Classification Search ............. 53/425, 53/426, 428, 431, 473, 477, 478, 111 R, 111 RC
See application file for complete search history.

(56) References Cited

U.S. PATENT DOCUMENTS

| | | | | |
|---|---|---|---|---|
| 4,512,865 A * | 4/1985 | Yamauchi | ............ | 204/271 |
| 5,129,999 A | 7/1992 | Holland et al. | | |
| 5,224,593 A * | 7/1993 | Bennett | ............ | 53/425 |
| 5,524,419 A * | 6/1996 | Shannon | ............ | 53/431 |
| 5,649,410 A * | 7/1997 | Martin et al. | ............ | 53/431 |
| 5,687,541 A | 11/1997 | Martin et al. | | |
| 5,706,634 A * | 1/1998 | Edwards et al. | ............ | 53/473 |
| 5,842,325 A * | 12/1998 | Godly et al. | ............ | 53/411 |
| 6,296,744 B1 | 10/2001 | Djeiranishvili et al. | | |
| 6,426,066 B1 * | 7/2002 | Najafi et al. | ............ | 424/78.04 |
| 6,528,214 B1 | 3/2003 | Pliner et al. | | |
| 6,632,347 B1 * | 10/2003 | Buckley et al. | ............ | 205/620 |
| 6,752,757 B2 | 6/2004 | Muir et al. | | |
| 2001/0022273 A1 * | 9/2001 | Popov et al. | ............ | 204/518 |
| 2002/0165431 A1 | 11/2002 | Muir et al. | | |
| 2002/0182262 A1 | 12/2002 | Selkon | | |
| 2003/0146108 A1 * | 8/2003 | Nakamura et al. | ............ | 205/705 |
| 2004/0055896 A1 | 3/2004 | Anderson et al. | | |
| 2004/0060815 A1 | 4/2004 | Buckley et al. | | |
| 2004/0208940 A1 | 10/2004 | Selkon | | |

FOREIGN PATENT DOCUMENTS

| | | |
|---|---|---|
| EP | 0 441 389 | 8/1991 |
| GB | 2 094 992 | 9/1982 |
| JP | 56-130713 A | 10/1981 |
| JP | 63-254417 A | 10/1988 |
| JP | 63254416 A * | 10/1988 |

(Continued)

OTHER PUBLICATIONS

European Search Report dated Oct. 1, 2010 for European Patent Application No. 07789583 (7 pages).

*Primary Examiner* — Stephen F Gerrity

(74) *Attorney, Agent, or Firm* — Holland & Hart LLP

(57) ABSTRACT

A method of sterilizing a contact lens includes at least partially sterilizing the contact lens with an application of electrolyzed brine. A system for at least partially sterilizing a contact lens in initial packaging includes a generator for producing electrolyzed brine with biocidal activity, and a dispenser for dispensing a quantity of electrolyzed brine from the generator into the initial packaging with the contact lens.

20 Claims, 3 Drawing Sheets

FOREIGN PATENT DOCUMENTS

| | | | |
|---|---|---|---|
| JP | 03-274524 A | 5/1991 | |
| JP | 03274524 | * 12/1991 | ...................... 53/425 |
| JP | 04-234724 A | 8/1992 | |
| WO | 97/20019 | 6/1997 | |
| WO | WO 03082445 A1 | * 10/2003 | ...................... 53/425 |
| WO | WO 2006115369 A1 | 6/2008 | |

* cited by examiner

METHODS AND SYSTEMS FOR CONTACT LENS STERILIZATION

RELATED APPLICATIONS

This application claims the benefit under 35 U.S.C. §119 (e) of U.S. Provisional Patent Application No. 60/759,735, filed Jan. 18, 2006 titled "Methods and Systems for Contact Lens Sterilization," which application is incorporated herein by reference in its entirety.

BACKGROUND

Due to the potential risk of infection, contact lenses are required to be supplied to the end user in a sterile state. The level of sterility required is governed by various U.S. Food and Drug Administration (FDA) guidelines and also European Standard EN 556. Both state that the theoretical probability of there being a viable micro-organism present on/in the lens must be equal to or less than $1\times10^{-6}$. This is often expressed as a Sterility Assurance Level (SAL) of $10^{-6}$ or 6 log.

This required level of sterilization is usually achieved by terminal sterilization, meaning that the lenses are sterilized at the end of the manufacturing and packaging process. The sterilization process typically involves some form of temperature and/or pressure-based sterilization technique. For example, the lens and a quantity of storage saline are sealed in a final shipping package and then subjected to a terminal sterilization process that typically involves heating the package in an autoclave to a temperature that insures sterilization.

Specifically, the packaged lens is sterilized by placing the package in an autoclave at an elevated humidity, temperature and pressure for an extended period of time, usually at least 15 minutes, and more typically 30 minutes, at 121° C. at a pressure of 1 atmosphere. In the case of lenses packaged in blister packs (the accepted method of packaging disposable contact lenses), there is the additional requirement to balance the pressure changes during heat-up and cool down to prevent the blister packages from bursting. This required balancing has the effect of prolonging the autoclave cycle.

Although this commercial process produces thoroughly sterilized contact lenses, the batch-wise autoclave sterilization step is time consuming, costly, and inefficient. It also detracts from the otherwise flow-line manufacturing process required to economically manufacture high volumes of disposable contact lenses, particularly for a daily-wear, disposable modality.

Amongst other negative effects of the autoclave process are the potential effects of the high temperature on the lens packaging and package contents. For instance, contact lens blister packages are generally fabricated from an injection molded polypropylene to form a boat that is closed with a laminated aluminum foil. Whilst polypropylene is relatively immune to the effects of the temperatures typically experienced in autoclave processing, some mechanical distortion may occur. This distortion is usually avoided by forming a relatively thick-walled boat or blister. While this generally prevents the distortion, it means that thin-walled packaging cannot be used even though the thin-walled packaging would be less-expensive and easier to work with.

Similarly, the temperature and pressure changes experienced during the autoclave process may cause some cosmetic deterioration of the foil used to close the boat. This often results in a slightly wrinkled foil. The effects of water applied at high temperature and pressure within the autoclave will also limit the use of pre-printed foils to inks compatible with the autoclave process. Currently, this limitation is generally overcome by means of an overlabel, which is applied to the lens pack after autoclaving, and hence adds another step to the manufacturing cycle.

The requirement for autoclaving may also complicate the use of certain saline additives, such as hyaluronic acid, due to hydrolysis at elevated temperatures. In the case of hyaluronic acid, hydrolysis during autoclaving resulting in an undesirable lowering of the mean molecular weight of the hyaluronic acid, along with an increase in its polydispersity.

The use of autoclaving also requires complex pressure equipment, and each autoclave load requires careful monitoring of the temperatures throughout the chamber. In the event of a failure to demonstrate that the required temperature within the chamber was held for the prescribed time to satisfy legal sterilization requirements or guidelines, the lenses will require re-autoclaving or scrapping. Such failures may occur due to a fault in the actual autoclave itself, or, more commonly, due to a failure of a temperature sensor within the autoclave.

Efforts have been made to avoid these disadvantages of the typical autoclave based terminal sterilization process. U.S. Pat. No. 4,464,336, for instance, teaches a method of sterilization utilizing an ultra-violet flash discharge to produce an intense pulse of UV light. Similarly, U.S. Pat. Nos. 5,034,235 and 4,871,559 disclose the use of intermittent, short-duration pulses of very intense light, containing both visible and ultra-violet frequencies to inactivate microorganisms on the surfaces of food products. U.S. Pat. No. 5,786,598 and U.S. Pat. No. 6,592,816 teach the application of this technology to the sterilization of contact lenses.

Whilst the teachings of U.S. Pat. Nos. 5,786,598 and 6,592,816 would allow for a flow-line manufacturing process, there are some important limitations with this approach. Firstly, if the contact lens contains a UV blocker, sufficient absorption of the incident ultraviolet light may occur so as to preclude the inactivation of microorganisms. Secondly, any method reliant upon irradiation of the lens and lens package contents will be less effective or entirely ineffective for a non-transparent package, such as disclosed in U.S. Patent Application Publication No. 200402383801.

SUMMARY

According to one exemplary embodiment, a method of sterilizing a contact lens includes at least partially sterilizing the contact lens with an application of electrolyzed brine.

Additionally, according to another of many exemplary embodiments, a system for sterilizing a contact lens in initial packaging includes a generator for producing electrolyzed brine with biocidal activity, and a dispenser for dispensing a quantity of electrolyzed brine from the generator into the initial packaging with the contact lens.

BRIEF DESCRIPTION OF THE DRAWINGS

The accompanying drawings illustrate various embodiments of the present system and method and are a part of the specification. The illustrated embodiments are merely examples of the present system and method and do not limit the scope of the claims.

Throughout the drawings, identical reference numbers designate similar, but not necessarily identical, elements.

DETAILED DESCRIPTION

Figure 1:
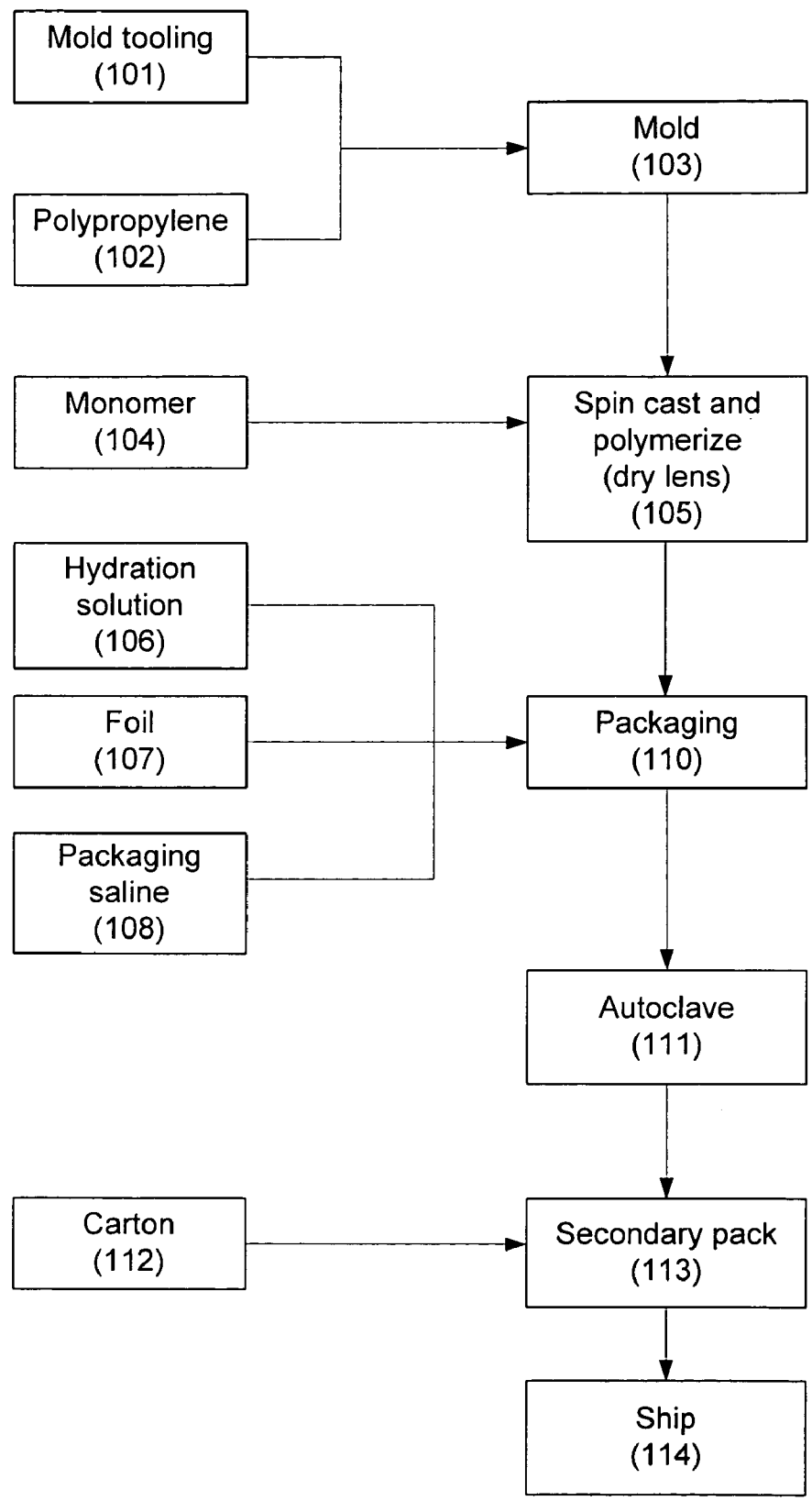
FIG. 1 illustrates a process of manufacturing contact lenses including an autoclave sterilization process, according to one exemplary embodiment.

This disclosure describes methods and system for the use of chemical sterilization in a manufacturing process for contact lenses. More specifically, this document described methods and systems for the use of an electrolyzed brine solution to sterilize contact lenses during manufacturing and packaging as a means to achieve a fully flow-line manufacture of the contact lenses, particularly daily disposable contact lenses. As used herein and in the appended claims, a "flow-line" process is a process with a continuous flow of product as opposed to a batch process in which product is divided into discreet batches for processing at one or more points in the production process.

The disadvantages of autoclaving and using UV and visible light to sterilize contact lenses may be overcome by packaging the contact lens in a solution containing an effective amount of a sterilizing agent or biocide. Many biocides have found application in contact lens care solutions intended for use by the patient during daily disinfection of traditional wear or frequent replacement lenses. Amongst these biocides are benzalkonium chloride (BAK), polyhexamine biguanide (PHMB), and chlorhexidine gluconate (CHG).

However, these biocides have not been used in the manufacture and initial packaging of contact lenses as a sterilizing agent because, when used in such an application, these conventional biocides produce adverse reactions, including pain, in some patients. For example, conjunctivitis may result from a hypersensitivity and reaction to traditional biocides if used on contact lenses. (See, van Ketel W G, Melzer-van Riemsdijk F A, "Conjunctivitis due to soft lens solutions," Contact Dermatitis. 6(5):321, 1980). Additionally, PHMB's have also been implicated in corneal staining with certain lens materials (See, Pritchard N., Young G., Coleman S., Hunt C. "Subjective and objective measures of corneal staining related to multi-purpose care systems," Contact Lens & Anterior Eye 26:3-9, 2003). BAK is also reported to be irritating to the eye in concentrations above 1:2000. (See, American Hospital Formulary Service. Volumes I and II. Washington, DC: American Society of Hospital Pharmacists, to 1984, p. 52:04.12).

Hydrogen peroxide-based lens disinfecting solutions, on the other hand, appear to be free of these and similar adverse patient reactions. Enzymes within biological structure, such as the tear film of the human eye, are capable of rapidly decomposing any peroxide present. However, the presence of even trace amounts of hydrogen peroxide on a lens surface is likely to cause significant pain to the wearer. Thus, peroxide-based care solutions require neutralization following disinfection, making then unworkable as a sterilizing agent in initial lens packaging.

Ozone has also been suggested as a suitable candidate for the in-pack sterilization of contact lenses in a manufacturing environment. U.S. Pat. No. 5,618,492 for instance discloses the flow-line sterilization of contact lenses by dissolving ozone in the packaging saline prior to sealing the pack. The residual ozone is then decomposed by irradiation with UV light, or by heat. However, the decomposition step then requires autoclaving or transparent packaging with all the attendant disadvantages described above.

Several other oxidizing biocides have been suggested for the sterilization/disinfection of contact lenses in a consumer environment as opposed to a manufacturing process. Typically, for sterilization applications after a lens is in use and subsequent to manufacturing, a lower level of biocidal activity is acceptable. FDA guidelines for consumer disinfecting solutions require a minimum 4 log reduction in viable bacteria, as opposed to the minimum 6 log reduction required in the manufacture of contact lenses.

U.S. Pat. No. 6,592,907, for instance, discloses a solution containing a chlorite salt along with a small quantity of hydrogen peroxide, suitable for both instillation into the eye, and for the disinfection of contact lenses. U.S. Pat. No. 5,252,291 discloses an electrolytic cell for use by the consumer for the routine disinfection of contact lenses. The contact lens is placed in the electrolytic cell along with saline, and the saline is the subjected to electrolysis, which liberates free chlorine. After a set period of time, the polarity of the cell is reversed in order to convert the chlorine back to chloride. However, these approaches do not provide the higher level of sterilization required in the manufacture of contact lenses Because of the various potentials for adverse reactions or other complications, the use of biocides has generally been avoided in the manufacture and initial packaging of contact lenses. Hence the reliance on autoclaving, despite its attendant disadvantages. However, as discovered by the Applicants, these problems with traditional biocides in contact lens manufacturing can be avoided by using electrolyzed brine as a sterilizing agent in initial contact lens packaging. As will be described herein, electrolyzed brine can provide the needed degree of sterilization and then decompose into an innocuous saline solution within hours or days of production. Similarly, the use of electrolyzed brine in combination with other traditional sterilization techniques can also provide the needed degree of sterilization while reducing, if not eliminating, dependence on the traditional sterilization techniques with their attendant disadvantages.

"Super-oxidized water" solutions have been known for several years to be potent biocides, and have found application in the purification of potable water (See GB 2,257,982, incorporated herein by reference), the disinfection of swimming pools and the treatment of liquid waste. These solutions are prepared by the electrolysis of sodium chloride solutions using specially designed cells in which the anodic and cathodic streams are separated by a semi-permeable membrane, and then blended to form the biocidal solution. The "super-oxidized water" itself contains many active species such as sodium hypochlorite and hypochlorous acid, and are typified by a high redox potential. Typically, these biocidal solutions are unstable, and decompose to harmless substances within hours or days of generation. Some elemental chlorine may also be produced, which will remain dissolved in the solution.

U.S. Pat. Nos. 6,296,744 and 6,632,347, which are incorporated herein by reference in their respective entireties, disclose an apparatus and methods for the electrolysis of a salt solution for use as a sterilizing solution, referred to herein as electrolyzed brine. The following additional patents and publications provide further information about the production of electrolyzed brine and are also incorporated herein by reference in their respective entireties: U.S. Pat. Nos. 6,752,757 and 6,528,214; and U.S. Patent Application Publication Nos. 20040208940, 20040060815, 20040055896, 20020182262, 20020165431 and 20010022273.

During the electrochemical process for producing electrolyzed brine, a continuous electrical current is passed through a sodium chloride solution between electrodes including an anode having positive polarity and a cathode having negative polarity. Under the action of the current in the liquid solution being processed, electrochemical reactions occur resulting in electrolysis products, such as active chlorine at the anode and sodium hydroxide at the cathode.

In order that the anodic and cathodic products do not become mixed through reciprocal chemical reactions during the electrochemical treatment process, a semi-permeable membrane or diaphragm is placed in the area between the electrodes. After the processing is complete the solution from both sides of the membrane is mixed to form the electrolyzed brine solution that can be used as a sterilizing or biocidal agent for a limited period of time. The resulting sterilizing agent has both anti-bacterial and anti-viral properties, including efficacy against a wide range of microorganisms including vegetative bacteria (gram positive and negative), fungi, viruses and bacterial endospores.

One application for the use of such a solution is the disinfection of medical instruments such as endoscopes. FDA 510(k) number k013280, for example, approves the use of such a generator and its resultant solution for the high level disinfection of instruments such as endoscopes. In this application, the generator is configured to produce a solution with approximately 200 ppm available chlorine. Such a solution will achieve a 6 log reduction in vegetative bacteria in 5-10 minutes. However, a somewhat weaker solution can be prepared for use with contact lenses as described herein. Too strong a solution could potentially have a deleterious effect on a contact lens if the exposure time is unduly prolonged.

Given enough time, reciprocal reactions return the electrolyzed solution to an aqueous sodium chloride solution. This decomposition will occur naturally within hours or perhaps days of the electrolysis.

To increase the amount of sterilizing agent produced by this process, a separate flow of sodium chloride solution may be passed through the reactor on both sides of the dividing membrane to produce a continuous stream of the two components, anodic and cathodic, that are then mixed to form the desired sterilizing or biocidal agent. In this way, a continuous flow of the desired sterilizing agent can be produced for a flow-line manufacturing process. As described herein, this basic process can be added to a flow-line manufacturing process for contact lens to provide the necessary sterilization for the lenses without requiring the traditional batch processing in an autoclave.

The relative concentrations of the active species present in the solution, and their attendant biocidal activity can be altered by varying the flow rate of salt solution passing over the electrodes, along with the current density applied to said electrodes. By judicious selection of these parameters, an active biocidal solution compatible with a contact lens may be produced. Whilst such a solution will have a lower biocidal activity, the desired 6 log reduction of viable microorganisms can still be met, albeit after a longer contact time Referring to FIGS. 1 and 2, a manufacturing and sterilization process for contact lenses typically includes the following. First, a mold (103) for the desired lens is produced. The mold (103) is typically produced of polypropylene (102) that may be shaped as needed through a mold tooling process (101).

A monomer mixture (104) is then injected into the mold (103) to form a hydrophilic contact lens. According to one exemplary embodiment, spin casting (105) may be used to form the monomer into the desired lens shape in the mold. The monomer mixture is then polymerized either thermally or photo-chemically. The material used may include 2-hydroxyethyl methacrylate (HEMA) or copolymers of glycerol monomethacrylate and HEMA, or methacrylic acid and HEMA.

Once formed, the lens may be packaged. The lens is first placed in its initial packaging (110). In some examples, the mold in which the lens was polymerized, which is essentially a plastic container, becomes part of the initial packaging with the lens remaining therein, such as described in WO 0130559 which is, incorporated herein by reference in its entirety. As used herein and in the appended claims, "initial packaging" refers to the packaging in which a contact lens is placed during or after manufacturing and in which it is transported to the patient or end user who then opens the initial packaging to access and wear the lens. Consequently, initial packaging is distinguished from any subsequent storage container that the lens may be placed in during the time it is used by the wearer.

The packaging (110) may also include a quantity of hydration solution (106) that is used by the wearer to wet the lens when the initial packaging is opened and before the lens is applied to the eye. In addition to any such hydration solution, the lens is typically packaged in a quantity of saline solution (108), also referred to as packaging solution, to maintain the lens in a moist state prior to initial use. The saline solution (108) is buffered with bicarbonate and may also contain a very small amount of a surfactant, such as poloxamer 407 to prevent the lens from sticking to the packaging.

As described above, the lens and packaging saline are typically placed in a container referred to as boat. The boat is then sealed with foil (107), for example, a laminated aluminum foil. According to one exemplary embodiment, the boat may be replaced with an additional laminated aluminum foil, as described in PCT/AU02/01105, which application is incorporated by reference herein in its entirety.

To this point, the production of the lens and lens packaging can be a flow-line process. However, in a conventional manufacturing process, as described above, the now packaged lenses would be sterilized in batches in an autoclave (111). The process and disadvantages of the autoclaving process are described above. Additionally, autoclaves have a tendency to malfunction or breakdown further complicating and elongating the manufacturing process.

Once sterilized, the packaged lens may be combined into a carton (112) or other container referred to as a secondary package (113). The secondary package (113) contains a quantity of identical or related lenses, e.g., for right and left eyes. Once in the secondary packaging (113), the lenses are ready for shipping (114), for example, directly to the customer or wearer.

The entire process illustrated in FIG. 1 can be implemented as a flow-line process with the exception of the autoclaving (111). Obviously, the introduction of a batch step in an otherwise flow-line process creates a potential bottleneck in the process. This possibility is avoided in the process illustrated in FIG. 2, in which the autoclaving sterilization process is replaced with the use of electrolyzed brine as an in-package sterilizing agent. Elements of the process illustrated in FIG. 2 that have already been described in connection with FIG. 1 will not be redundantly described.

Figure 2:
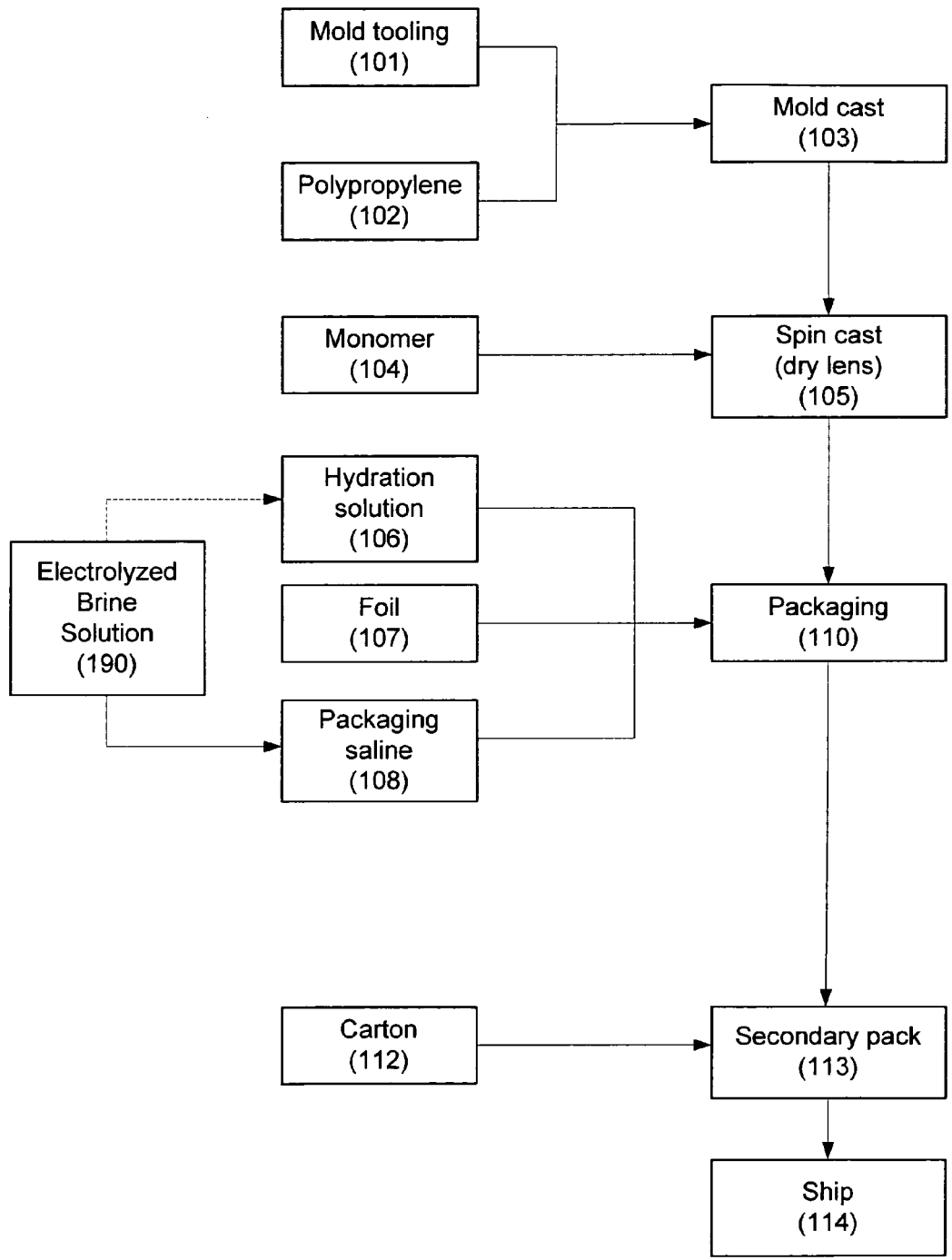
FIG. 2 illustrates a process of manufacturing contact lenses, according to one exemplary embodiment, including a sterilization process using electrolyzed brine according to principles described herein.

Referring to FIG. 2, an electrolyzed brine solution (190) is added to the packaging saline (108) used to initially package the lens. In some other examples, however, rather than adding the electrolyzed brine solution to other packaging saline, the electrolyzed brine is used as the exclusive packaging solution for the lens.

The electrolyzed brine (190) will act as a sterilizing agent or biocide to sterilize both the lens and the packaging saline (108) to the degree required by applicable legal requirements and guidelines. The electrolyzed brine (190) will then naturally decompose over a matter of hours or days into additional saline solution. Thus, by the time the user receives the lens packaging and opens and wears the lens, the electrolyzed brine will be essentially saline solution in the packaging saline. Thus, there is no potential for any adverse patient reaction to the electrolyzed brine (190) used to sterilize the packaged lens.

In some cases, the lens may also include a handling tint, for example, an anthroquinone dye. These tints are color-fast in hypochlorite solutions below 100 ppm free chlorine. Some elemental chlorine will also be present within the electrolyzed brine, but by judicious control of the operating parameters of the generator used to produce the electrolyzed brine the levels of chlorine will be essentially that found in many potable water supplies. Limiting the amount of chlorine produced may increase the time required to sterilize the packaged lens, but will also prevent bleaching of any tinting of the lens, limit any noticeable chlorine odor and preserve the mechanical or tensile strength of the lens.

As shown in FIG. 2, the electrolyzed brine solution (190) may also, in some examples, be added to the hydration solution (106) packaged with the lens. This will serve to insure the sterility of the hydration solution, again without any potentially adverse impact on the user.

Looking earlier in the process illustrated in FIG. 2, following polymerization (105), the contact lens may be subjected to hydration and other processing steps, such as quality inspection. This processing may also include an initial step in the overall sterilization technique. For example, the newly-formed, dry lenses may be passed under a germicidal ultraviolet lamp into a controlled environment (e.g. HEPA filtered laminar flow hood) to begin the sterilization of the lens before the lens is hydrated and packaged.

The lens and packaging saline, including the electrolyzed brine, are then placed in the packaging (110) and sealed, for example, with foil (107). According to one exemplary embodiment, the electrolyzed brine in the package provides sufficient biocidal activity that there is no need to autoclave the package. Rather, the packaged lens can move directly on to placement in the secondary packaging (113) and subsequent shipping (114). Consequently, the manufacturing process illustrated in FIG. 2 can be an entirely flow-line process. This significantly increases the possible rate of lens production by omitting the batched autoclaving process.

Additionally, the heat used to seal the foil (107) to the packaging (110) may also serve to, at least in part, sterilize the lens, providing a level of biocidal activity. According to another exemplary embodiment, the electrolyzed brine in the package may be formulated to achieve sterility assurance levels of approximately $10^{-3}$ or $10^{-4}$. In such a case, the heat used to seal the foil (107) to the packaging (110) may complete the sterilization of the lens to the desired degree ($10^{-6}$). The heat used to seal the foil (107) will also likely increase the rate at which the electrolyzed brine decomposes into an innocuous saline solution. Given the relatively small amount of saline in the packaging and the prolific thermal conductivity of the foil, the heat used to seal the foil to the packaging may, according to one exemplary embodiment, raise the temperature of the electrolyzed brine and the saline to approximately 100° C. or more. This raise in temperature may cause an increase in the decay rate of the electrolyzed brine. An increase in the decay rate may cause the electrolyzed brine to be more active due to chemical kinetics. Consequently, according to one exemplary embodiment, the rate of biocidal activity increases with temperature. According to this embodiment, the electrolyzed brine, in combination with the heat used to seal the foil (107) to the packaging (110) can provide sufficient biocidal activity to achieve a sterility assurance level of at least $10^{-6}$.

Figure 3:
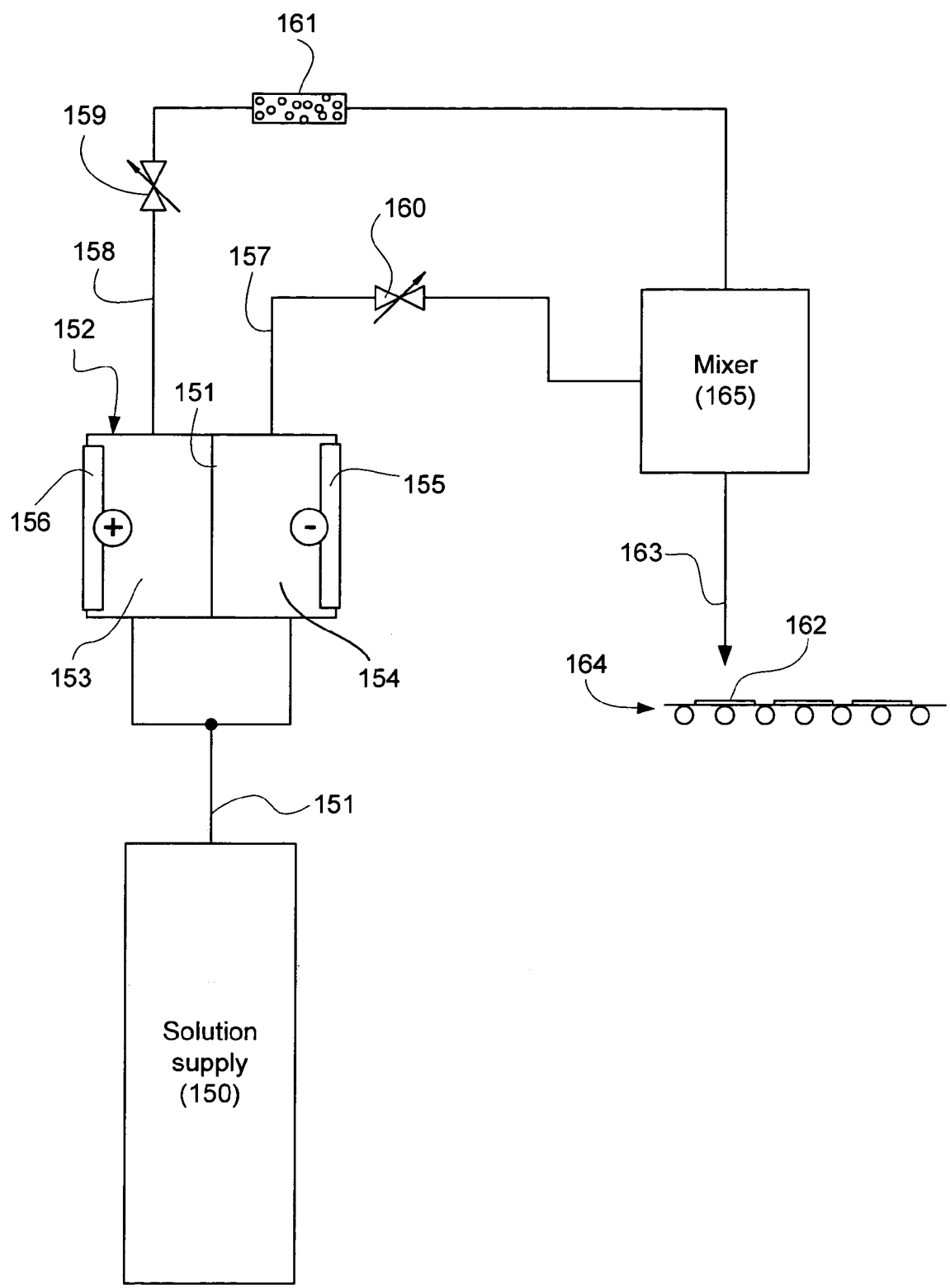
FIG. 3 illustrates a portion of a flow-line manufacturing process for contact lenses incorporating electrolyzed brine as a sterilizing agent according to one exemplary embodiment of the principles described herein.

FIG. 3 illustrates a portion of a flow-line manufacturing process for contact lenses incorporating electrolyzed brine as a sterilizing agent. As shown in FIG. 3, a supply of brine or sodium chloride solution (150) is provided. This supply can be of any size, and, specifically, may be large enough to provide for the uninterrupted production of electrolyzed brine during a run of contact lens manufacture. The supply (150) may include quantities of sodium chloride that are added in a metered fashion into a flow of water to provide the aqueous sodium chloride needed for the production of electrolyzed brine.

The water used may be softened or purified water, although purified water is not required and a tap water feed may be used. If purified water is used, the water may be purified by a combination of filtering and exposure to germicidal ultraviolet radiation. If the generator (152) needs a degree of conductivity to internally buffer the solution pH, a low concentration of a salt, preferably sodium hydrogen carbonate can be added to the purified water through an on-line mixer to the feed-line for the purified water. In a contact lens packaging application as described herein, sodium bicarbonate can be added, but is not required to be added to the feedwater stream and will serve as a buffering agent in the final solution.

In some examples, the supply (150) may include any number of separate reservoirs of solution or containers of sodium chloride. With a number of separate reservoirs or containers of material, an exhausted reservoir or container can be replaced with a full one, while another of the reservoirs or containers feeds the uninterrupted process. In this way, the uninterrupted periods during which the flow-line manufacturing process is conducted can be extended indefinitely subject only to such infrequent eventualities as breakdown, routine maintenance and/or materials shortage.

In the illustrated example, the aqueous solution is provided from the supply (150) through a supply line (151) to a generator (152). In other examples, the supply may be integrated into the generator (152) so that the generator receives a flow of water, e.g., purified water, and a supply of chemicals, e.g., salt that is provided using a conductivity control mechanism, to produce the brine solution within the generator that the generator then electrolyzes.

The generator (152) electrolyzes the brine solution in the manner described above. Specifically, the generator (152) is divided into two chambers, an anode chamber (153) and a cathode chamber (154) between which an electric current flows to electrolyze the brine solution in the generator (152).

A divider (151), for example, a semi-permeable membrane (151) separates the generator (152) into the anode chamber (153) and cathode chamber (152). The divider (151) allows electric current to flow between an anode (156) in the anode chamber (153) and a cathode (155) in the cathode chamber (154). However, the divider (151) resists the mixing of electrolyzed solutions from the two chambers. The divider (151) may include, for example, a porous membrane made of a ceramic based on zirconium oxide.

The supply line (151) supplies brine solution separately to both the anode chamber (153) and the cathode chamber (154). As described above, the current flowing through the generator (152) between the anode (156) and cathode (155) produces electrolysis products such as active chlorine at the anode and sodium hydroxide at the cathode.

The anode solution then flows from the anode chamber (153) through a flow line (158). In some embodiments, it may be desired to remove some of the chlorine or other electrolysis products from the anode solution. Consequently, a midstream catalytic reactor (161) may be provided through which the anode solution flows. The midstream catalytic reactor (161) may include a granulated catalyst or a sorbent for removal (e.g., chemical breakdown and/or sorption) of the active chlorine in the anode solution.

Similarly, the cathode solution flows from the cathode chamber (154) through a flow line (157). The anode and cathode solutions are then recombined in a mixer (165). Valves (159 and 160) may be included respectively in the anode flow line (158) and the cathode flow line (157) to regulate the timing and/or ratio of the anode and cathode solutions entering the mixer (165).

In some examples, the mixer (165) may be omitted and the generator (152) may include a mixing mechanism for combining the solutions from the anode chamber (153) and cathode chamber (154). Thus, in some examples, the supply (150) and/or the mixer (165) may be integrated into the generator (152).

Once the anode and cathode solutions are recombined in the mixer (165), the mixture is referred to as electrolyzed brine or super-oxidized water and has the desired sterilizing and biocidal properties described herein. The electrolyzed brine may have a pH ranging from 7.20 to 7.70. Also as described, once mixed, the electrolysis products in the electrolyzed brine will begin to react and decompose, producing an innocuous saline solution. This decomposition may take 2 to 12 hours or more depending on conditions. During the time that the electrolyzed brine is still effective as a sterilizing agent, it is used to package and sterilize contact lenses in a manufacturing process (164) such as that described in connection with FIG. 2.

FIG. 3 illustrates the generator (152) for the electrolyzed brine in a general form. However, there are a variety of specific configurations that the generator (152) may take. For example, GB 2253860, which is incorporated herein by reference in its entirety, describes two electrodes, one of which is a rod and the other a cylinder. The electrodes are coaxially-arranged to provide anode and cathode (working and auxiliary) flow chambers which are separated by a porous membrane.

Water is fed from the bottom to the top of the device through the working chamber. Simultaneously, water having a higher mineral content flows through the auxiliary chamber to a gas-separating chamber. An electric current is passed between the cathode and anode through the water in both chambers and the porous membrane separating the chambers. Water flowing through the auxiliary chamber recirculates to the auxiliary chamber by convection and by the shearing forces applied to the water through the rise of bubbles of gas which are generated on the electrode in the auxiliary chamber. The pressure in the working chamber is higher than that in the auxiliary chamber, and gaseous electrolysis products are vented from the gas-separating chamber by way of a gas-relief valve. A change of working mode from cathodic to anodic water treatment is achieved by changing polarity.

Any configuration for a generator producing electrolyzed brine may be used according to the principles described herein in a system or method for sterilizing contact lenses.

As shown in FIG. 3, a dispenser (163) will provide electrolyzed brine from the mixer (165), or an integrated mixer/generator, into each of a series of contact lens packages (162) moving through the manufacturing process (164). This dispenser (163) may include Hamilton motor-driven syringes used to ensure that an accurate quantity of solution is added to each lens package (162). The quantity of solution added to each lens package may range from, for example, 0.15 ml to 6 ml.

Lenses packaged in the electrolyzed brine will be sterilized to the degree required by applicable laws and safety guidelines before the electrolyzed brine decomposes into a simple saline solution. The decomposing saline solution may include some byproducts of the electrolysis such as hypochlorous acid, hypochlorite, and chlorates.

The surfactant used in the packaging solution that prevents the lens from sticking to the packaging may be added to the solution in the supply (150) and be processed through the generator (152). Alternatively, the surfactant can be added to the solution in the generator (152) or subsequent to the generator (152), such as before, after or in the mixer (165). Any additives desired in the packaging solution that are incompatible with the generator (152) can be added to the solution after the solution is output by the generator (152) and before the solution is introduced into the packaging (162).

In still another alternative embodiment, the surfactant can be added to the materials used to form the contact lens. The surfactant will then not have to pass through the generator (152), but will leach out of the lens during storage prior to initial use so as to be present to prevent the lens from sticking to the packaging as desired. In this case, the surfactant serves a dual function by prevent adhesion to the packaging as well as serving as a mold release agent to speed up hydration of the lens.

The electrolyzed brine has been demonstrated to meet the requirements for both sterilization and high level disinfection. A chemical sterilizing agent must be capable of achieving a 6 log reduction of viable microorganisms plus spores within a set period of time, whereas a high level disinfectant need not demonstrate sporicidal activity. Typically the recommended contact time for high level disinfection is shorter than that required for sterilization. In the case of the electrolyzed brine, high level disinfection may be achieved in 10 minutes, and sterilization in 20 minutes.

Two specific examples of using electrolyzed brine as a sterilizing agent within the initial packaging for contact lenses will be given below.

Example 1

A commercial electrolysed brine generator is configured to produce a biocidal solution as described in US patent application 2004/055896, incorporated herein by reference in its entirety. This solution has a sodium chloride concentration of 0.26% w/w, and an available free chlorine content of 220 ppm (as hypochlorous acid and sodium hypochlorite), with a pH between 6.00 and 6.20 (see Table 1 below)

The biocidal solution is then mixed with an equal volume of an auxiliary buffered saline solution to produce a sterilising lens packaging solution containing 0.6% sodium chloride and 110 ppm available chlorine, with a pH of 7.2. The actual compositions of these solutions are shown in Table 1

TABLE 1

| | Electrolyzed brine solution | Auxiliary saline solution | Packaging solution |
|---|---|---|---|
| Sodium chloride | 0.26 | 0.94 | 0.6 |
| Sodium hydrogen carbonate | n/a | 0.084 | 0.042 |

TABLE 1-continued

|  | Electrolyzed brine solution | Auxiliary saline solution | Packaging solution |
|---|---|---|---|
| Boric acid | n/a | 0.124 | 0.062 |
| sodium phosphate monobasic | n/a | 0.028 | 0.014 |
| Available free chlorine | 220 | n/a | 110 |
| Estimated pH | 6.2 | 7.4 | 7.2 |

Example 2

A commercial electrolyzed brine generator is configured to directly produce a packaging solution containing sodium chloride (0.6%). The generator is fed with a solution of sodium bicarbonate (0.05%) in purified water. By judicious adjustment of the solution flow rate through the generator, an available free chlorine content of about 100 ppm may be produced. This solution may be used directly to package a contact lens.

The preceding description has been presented only to illustrate and describe embodiments of the exemplary systems and methods. It is not intended to be exhaustive or to limit the systems and methods to any precise form disclosed. Many modifications and variations are possible in light of the above teaching.

What is claimed is:

1. A method of sterilizing an unused contact lens to a Sterility Assurance Level (SAL) of $10^{-6}$ comprising:
   sterilizing said unused contact lens with an application of electrolyzed brine as an in-package sterilizing agent;
   wherein said electrolyzed brine is sealed with said unused contact lens in an initial packaging of said contact lens.

2. The method of claim 1, further comprising heating said initial packaging to seal a foil to a container housing said contact lens and electrolyzed brine, wherein said heating is effective to at least partially sterilize said lens.

3. The method of claim 2, wherein said heating is further effective to promote decomposition of said electrolyzed brine.

4. The method of claim 2, wherein said container comprises a boat.

5. The method of claim 2, wherein said container comprises a laminated aluminum foil.

6. The method of claim 1, further comprising adding a surfactant to said electrolyzed brine after said brine is electrolyzed to prevent said contact lens from adhering to said initial packaging.

7. The method of claim 1, wherein a material used to form said contact lens contains a surfactant which leaches into said electrolyzed brine to prevent said contact lens from adhering to said initial packaging.

8. The method of claim 1, wherein said electrolyzed brine also contains a pH buffer.

9. The method of claim 1, further comprising autoclaving said initial packaging to further sterilize said contact lens.

10. A system for sterilizing a new contact lens in initial packaging to a Sterility Assurance Level (SAL) of $10^{-6}$, said system comprising:
    a generator for producing electrolyzed brine with biocidal activity; and
    a dispenser for dispensing a quantity of electrolyzed brine from said generator into said initial packaging with said new contact lens.

11. The system of claim 10, wherein said generator comprises a mixer that mixes salt with water to produce a brine solution that is then electrolyzed by said generator.

12. The system of claim 10, wherein said generator comprises an anode chamber and a cathode chamber separated by a membrane with a system for delivering a quantity of brine solution into each of said anode chamber and said cathode chamber.

13. The system of claim 10, wherein said generator is configured to produce said electrolyzed brine with a pH between 7.20 and 7.70.

14. The system of claim 10, wherein said electrolyzed brine is configured to decompose to an innocuous saline solution in between 2 and 12 hours from generation.

15. A method of sterilizing a contact lens comprising:
    generating a quantity of electrolyzed brine;
    placing said electrolyzed brine in a dispenser;
    disposing a newly manufactured contact lens in a contact lens package;
    presenting said contact lens package containing said newly manufactured contact lens adjacent to said dispenser; and
    dispensing a quantity of said electrolyzed brine from said dispenser into said contact lens package to at least partially sterilize said contact lens with said dispensed electrolyzed brine.

16. The method of claim 15, further comprising heat sealing said contact lens in a primary package;
    wherein said heat sealing enhances a rate of biocidal activity of said electrolyzed brine.

17. The method of claim 15, further comprising:
    packaging said contact lens within a package; and
    passing said packaging and said contact lens through an autoclave to further sterilize said contact lens.

18. The method of claim 15, further comprising packaging said contact lens and said electrolyzed brine in a contact lens package, wherein said application of said electrolyzed brine and said packaging of said contact lens in said contact lens package comprises a flow-line process.

19. The method of claim 15, further comprising adding a bicarbonate to said electrolyzed brine.

20. The method of claim 15, wherein said electrolyzed brine dispensed into said contact lens package containing said newly manufactured contact lens sterilizes said newly manufactured contact lens to a Sterility Assurance Level (SAL) of $10^{-6}$.

* * * * *